United States Patent [19]

Sharpe et al.

[11] Patent Number: 5,300,082
[45] Date of Patent: Apr. 5, 1994

[54] ENDONEEDLE HOLDER SURGICAL INSTRUMENT

[75] Inventors: Leslie A. Sharpe, Edina, Minn.; Francis C. Peterson, Prescott, Wis.

[73] Assignee: Sharpe Endosurgical Corporation, Minneapolis, Minn.

[21] Appl. No.: 818,072

[22] Filed: Jan. 8, 1992

[51] Int. Cl.$^5$ .................................... A61B 17/00
[52] U.S. Cl. ................................ 606/147; 606/208
[58] Field of Search ............ 606/223, 224, 147, 148, 606/208

[56] References Cited

U.S. PATENT DOCUMENTS

| | | | |
|---|---|---|---|
| 1,539,221 | 5/1925 | Tennant . | |
| 3,038,475 | 6/1962 | Orcutt | 606/222 |
| 3,160,157 | 12/1964 | Chisman | 606/223 |
| 3,398,746 | 8/1968 | Abramson | 606/147 |
| 3,828,791 | 8/1974 | Santos . | |
| 3,835,860 | 9/1974 | Garretson . | |
| 4,058,126 | 11/1977 | Leveen . | |
| 4,414,908 | 11/1983 | Eguchi et al. | 606/148 |
| 4,440,170 | 4/1984 | Golden et al. | 606/142 |
| 4,572,185 | 2/1986 | Rich | 606/147 |
| 4,602,631 | 7/1986 | Funatsu | 606/142 |
| 4,614,187 | 9/1986 | Mulhollan et al. | 606/148 |
| 4,621,640 | 11/1986 | Mulhollan et al. | 606/148 |
| 4,759,364 | 7/1988 | Boebel | 606/139 |
| 4,989,157 | 2/1990 | Messroghli et al. | 606/147 |
| 5,015,250 | 5/1991 | Foster | 606/148 |
| 5,100,432 | 3/1992 | Matsutani | 606/223 |
| 5,127,918 | 7/1992 | Boebel | 606/208 |
| 5,133,724 | 7/1992 | Wilson et al. | 606/208 |
| 5,156,608 | 10/1992 | Troidl et al. | 606/142 |

OTHER PUBLICATIONS

Endoscopic Curved Needle Driver, Cook Surgical.
Endoscopic Instruments, Cook Urological, a Cook Group Company, Endoscopic Curved Needle Driver.
Pre-Market Notification, Sharpe Endoneedle Holder.

Primary Examiner—Stephen C. Pellegrino
Assistant Examiner—Gary Jackson
Attorney, Agent, or Firm—Merchant, Gould, Smith, Edell, Welter & Schmidt

[57] ABSTRACT

A surgical instrument having a surgeon operable control handle for grasping surgical needles or other objects. The instrument has a moveable jaw opposed to a fixed jaw. The control handle engages a clamping spring which closes the jaws and exerts a grasping force which is proportional to the size of the object located between the jaws.

8 Claims, 5 Drawing Sheets

FIG. I

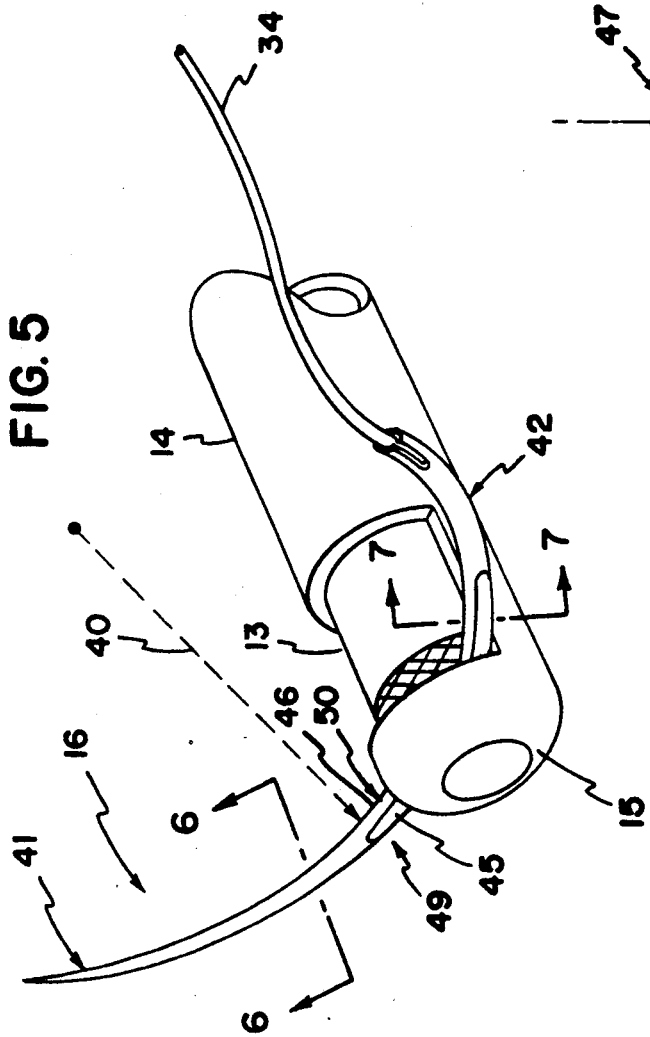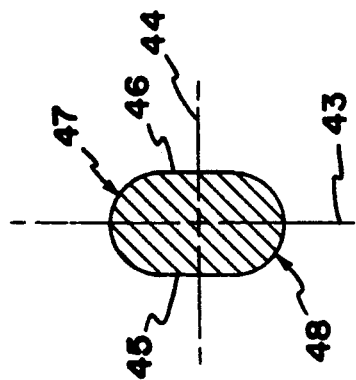

ENDONEEDLE HOLDER SURGICAL INSTRUMENT

BACKGROUND OF THE INVENTION

1. Field of the Invention

The present invention relates to surgical instruments for use during laparoscopic surgery. More particularly, the invention is directed to a needle holder for use inside the abdominal cavity.

2. Description of the Prior Art

The typical laparoscopic surgical procedure begins with the puncture of the patient's abdominal wall and the placement of an access port. Next, gas is admitted to the abdominal cavity partially inflating it, forming a pneumoperitoneum. A laparoscope or endoscope is next inserted through the access port to permit viewing of the organs during the surgical procedure. Typically the laparoscope has both an eyepiece and a video monitor to permit visualization of the surgical field by the surgeon. Additional access ports may be located elsewhere on the abdominal wall to permit insertion of surgical instruments into the operating field. Access ports come in a variety of diameters and 5, 7 and 11 millimeter ports are widely used for surgery within the peritoneal cavity. Surgical instruments for use through such ports are readily available to surgeons specializing in endoscopic surgery.

Many endoscopic surgical procedures require the use of surgical needles within the abdominal cavity. Typically a needle with an attached suture will be passed through an access port into the abdominal cavity. Next a grasping tool such as a SEMM Needle Holder will be passed through a port and the needle will be positioned within the jaws of the needle holder. The surgeon can manipulate the needle with the needle holder to pass the needle through tissue planes in preparation for ligation. Prior art needle holders such as the SEMM Needle Holder have diverging jaws and a scissors-like handle which limits the amount of grasping force which can be applied to the needle. This prior art device is difficult to use with large needles which have a tendency to slip in the jaws.

BRIEF SUMMARY OF THE INVENTION

In contrast to the traditional needle holder the present invention supplies a grasping force which is proportional to the size of the object placed between the jaws of the instrument. Structurally, the endoneedle holder has a surgeon operated control handle which can be manipulated to open and close the jaws. The control handle includes a rear grip and a foregrip which are nested together. Preferably the rear grip lies in the surgeons palm and slides into the foregrip as the surgeon squeezes the control handle. Motion of the rear grip causes a moveable jaw member to move into engagement with a fixed jaw member. The moveable jaw member moves in a linear as opposed to an arcuate path. The rear grip itself is coupled to a clamping spring which in turn engages the moveable jaw member. When the rear grip is fully depressed the grips engage a lock member. The grips are retained in a locked position until a lock button is depressed releasing the grips. Thus placement of a needle or other object between the fixed jaw member and the moveable jaw member will define the "jaw space" and continued motion of the rear grip into the foregrip will cause the clamping spring to deflect until the grips are latched together. In this fashion jaw spacing controls spring deflection which in turn defines the holding force. This holding force is proportional the size jaw space. The principal advantage of this architecture is to permit the instrument to grasp "thin" and therefor presumably fragile structure with a "light" holding force and to permit the tool to grasp "large" and therefore presumably robust objects with a "heavy" holding force.

BRIEF DESCRIPTION OF THE DRAWING

Throughout the several figures of the drawing like reference numerals are used to identify identical structure, wherein:

FIG. 5 is a perspective view of the endoneedle holder grasping a preferred curved needle;

FIG. 6 is a cross-section of the distal end of the preferred needle; and,

FIG. 7 is a cross-section of the preferred needle where the needle is grasped by the endoneedle holder.

DETAILED DESCRIPTION OF THE EXEMPLARY EMBODIMENT

Figure 1:
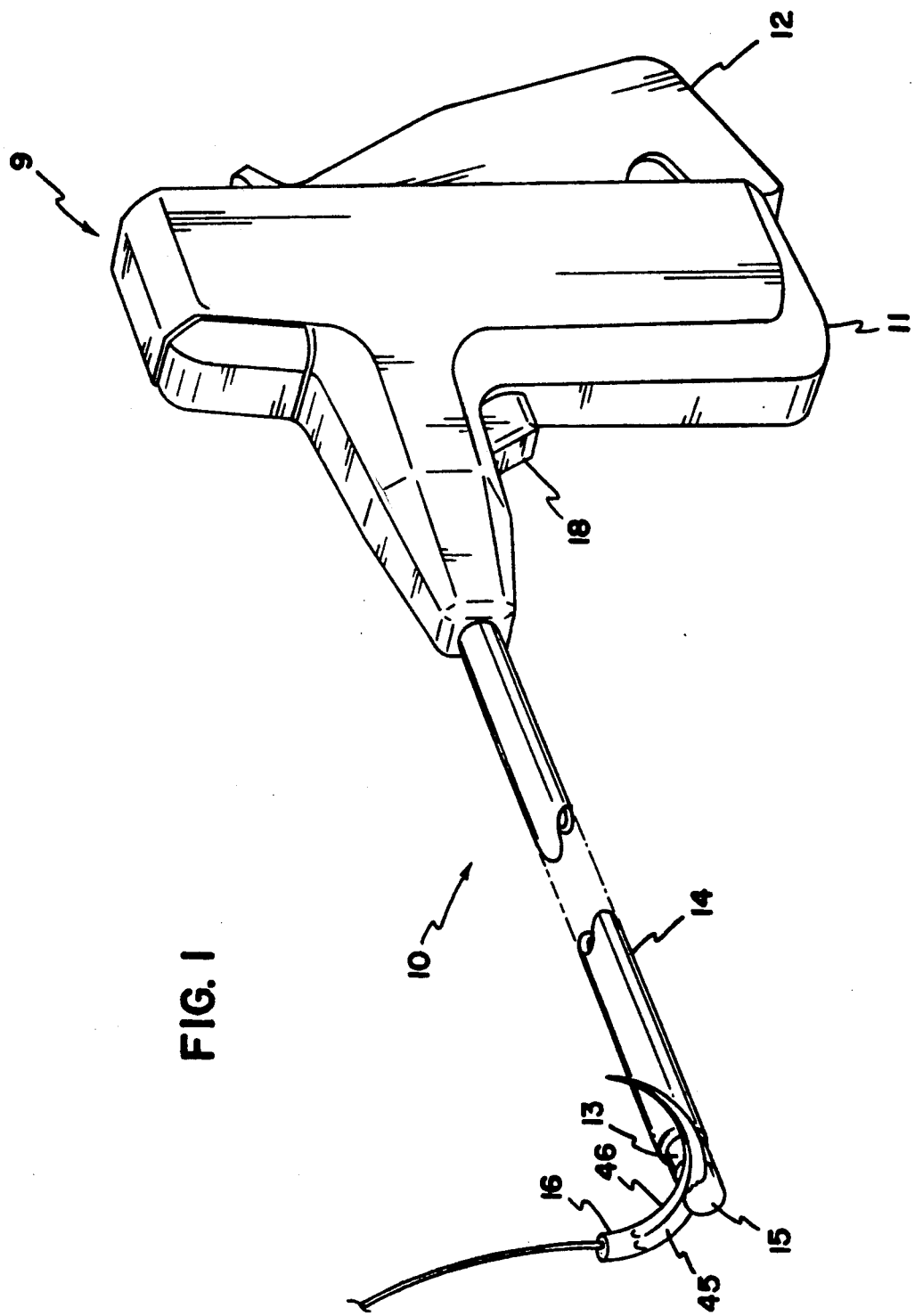
FIG. 1 is a perspective view of the assembled surgical instrument.

FIG. 1 is a perspective view of the endoneedle holder 10. The instrument includes a control handle 9 attached to an extended sheath 14. At the end of the sheath 14 there is a fixed jaw 15. The moveable jaw 13 moves along the axis of the lumen of the sheath 14. The control handle 9 has a moveable rear grip 12 and a fixed foregrip 11. The foregrip 11 is molded of a plastic and attached to the stainless steel tubular sheath 14. A moveable release button 18 is mounted within the foregrip 11. The rear grip 12 is adapted to slide into the foregrip 11 controlling closure of the moveable jaw member 13 against the fixed jaw member 15 which is anchored to the sheath 14. The depth of the jaws extends to approximately half the diameter of the sheath 14. The overall length of the sheath is approximately 30 cm while the preferred diameter of the sheath is approximately 6.5 mm. In FIG. 1 the jaws are positioned against the sides of a curved needle 16 which may have slightly flattened sides 45 and 46 to index the needle in the jaws. It is preferred to have the opposed jaw surfaces parallel to each other. The jaw faces are preferably cut with a diamond pattern to enhance holding power. The jaw faces are preferably perpendicular to axis of the sheath, although other jaw geometries are contemplated within the scope of the invention.

Figure 2:
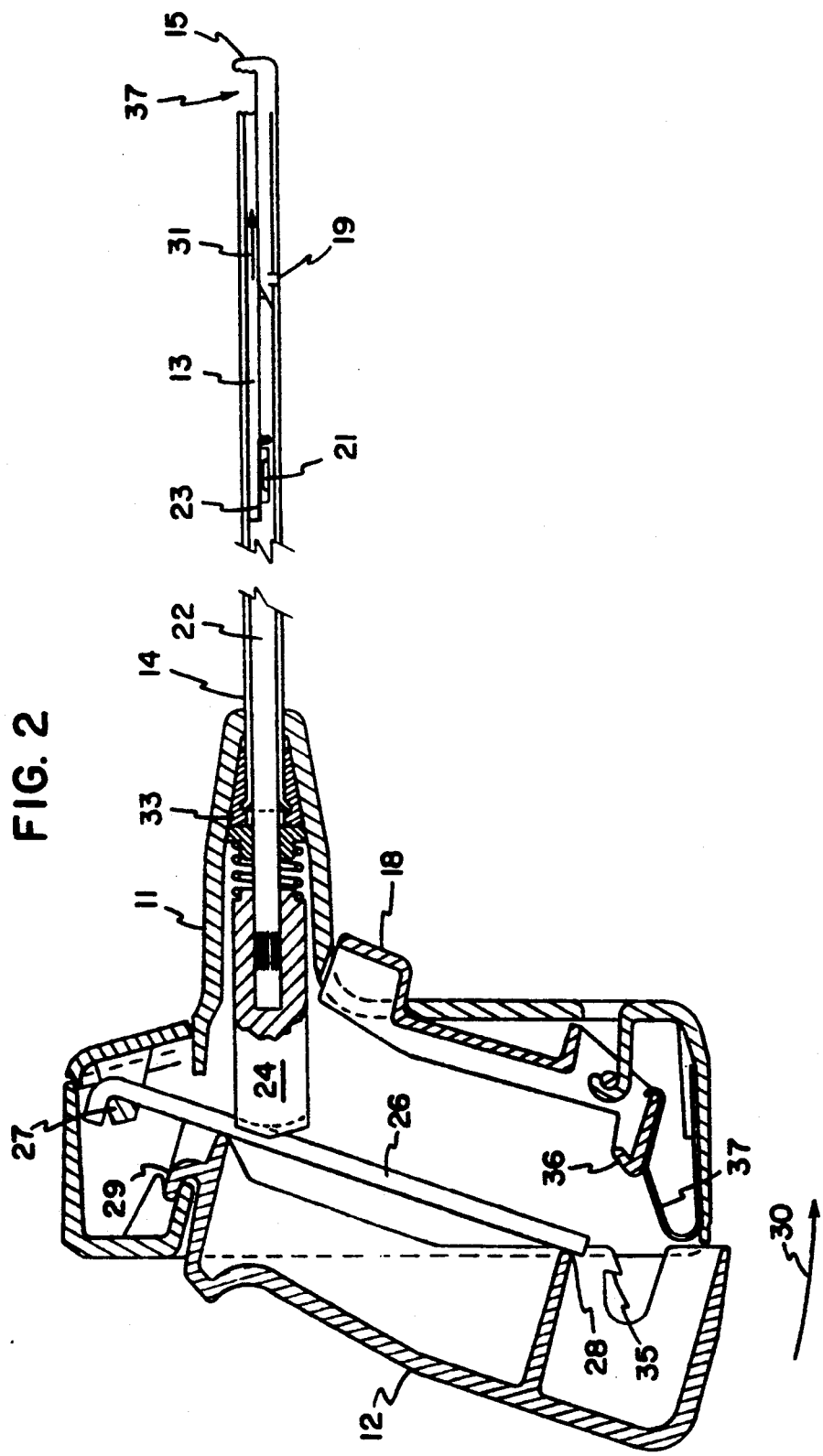
FIG. 2 is a cross-section of the surgical instrument depicting the jaws in the open position.

FIG. 2 shows a crossection of the endoneedle holder instrument 10, with the jaws fully opened. The fixed jaw 15 has a tang 19 mated to a complimentary tang receiving aperture 20 formed in the sheath 14. These structures together anchor the fixed jaw member 15 in the sheath 14 during use but permit removal of the fixed jaw member 15 from the sheath 14 for cleaning or replacement. The movable jaw member 13 has complimentary semicircular cross-sectional shape to guide the movable jaw member 13 into engagement with the fixed jaw member 15. A plug 21 formed in the movable jaw member 13 permits attachment to a slot 23 formed in the push rod 22. The metal push rod 22 is molded onto a plastic guide rod 24. The rear end of the guide rod 24 has molded channel feature 25 which engages the clamping spring 26. A helical restoring spring 32 is positioned between the foregrip 11 and the guide rod 24 to ensure that the push rod 22 follows the motion of the rear grip 12. A gas seal 33 encircles the push rod 22 at the end of the sheath 14 to seal the instrument against loss of gas from the abdominal cavity and to maintain the sterility of the operating field.

One end of the clamping spring 26 is pivotally mounted in the foregrip 11 at a pivot point 27 while the other end of the clamping spring 26 engages a reception feature 28 formed the rear grip 12. The rear grip 12 itself is pivotally mounted in the foregrip 11 at pivot point 29. Thus motion of the rear grip 12 along arcuate path 30 causes the clamping spring 26 to move the guide rod 24 and push rod 22 toward the fixed jaw 15 indicated by path 31. Together the fixed jaw 15 and the moveable jaw 13 define a "jaw space" 37 between the jaws.

Figure 3:
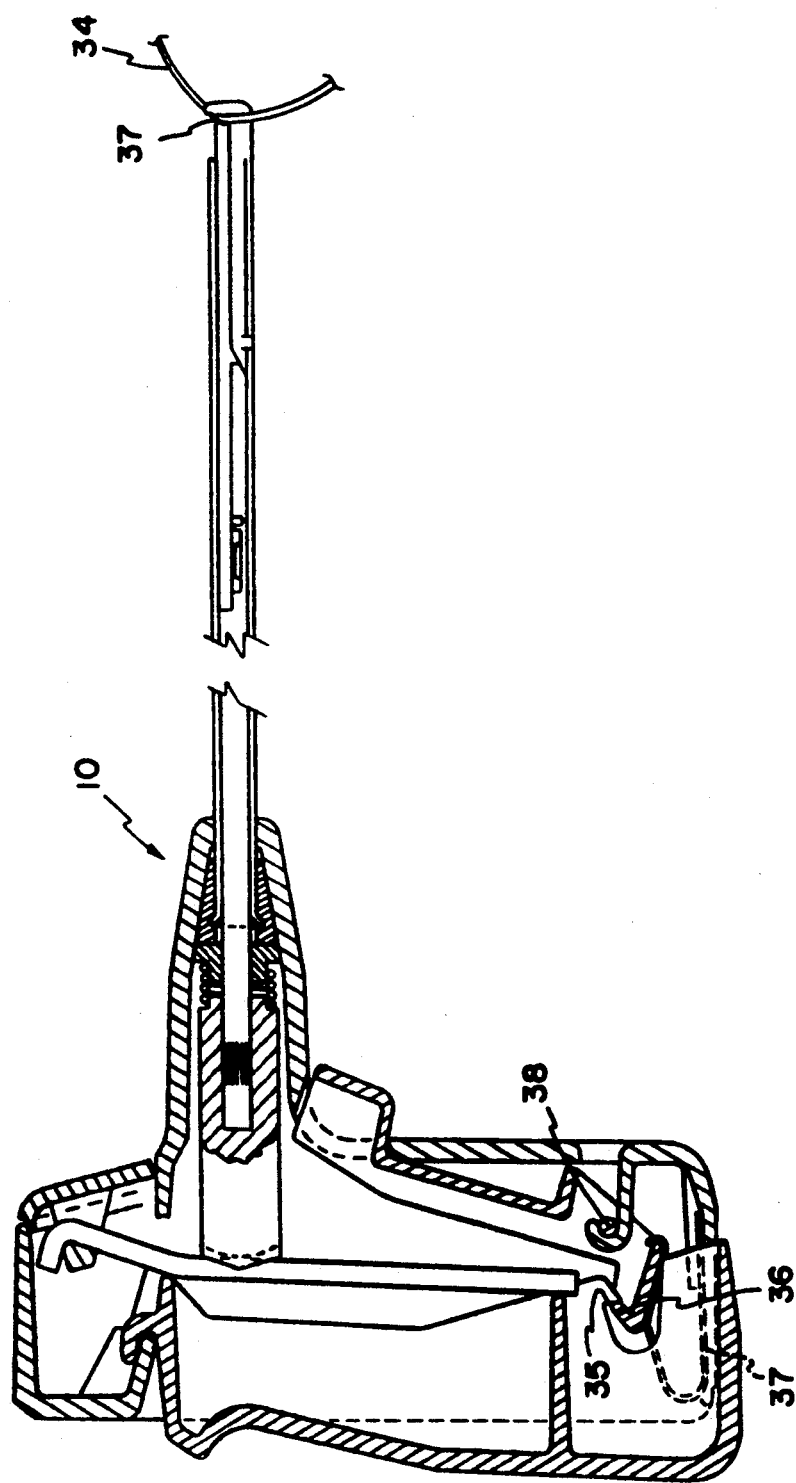
FIG. 3 is a cross-section of the surgical instrument depicting the jaws closed on a suture.

FIG. 3 shows the instrument 10 with the jaws 13 and 15 closed onto a thin piece of suture or ligature 34, located in the jaw space 37. In this figure the rear grip 12 is locked in engagement with the foregrip 11 by the engagement of latch hook 35 formed on the rear grip 12 with the latch hasp 36 formed on the lock button member 18. This lock button member 18 is pivotally mounted within the foregrip 11 and can move about pivot point 38. In use, the surgeon can depress the release button 18 causing the lock button member to pivot about point 38 disengaging the latch has 36 from the latch hook 35 unlocking the foregrip 11 from the rear grip 12. Usually the surgeon will squeeze the grips together to facilitate operation of the lock button. A bias spring 37 is mounted between the lock button member and the foregrip to bias the latch hasp 36 so that squeezing the rear grip 12 into the foregrip 11 will automatically engage the lock structures. The motion of the lock button member 18 will provide a tactile and auditory confirmation of the locking action to the surgeon.

In FIG. 3 the ligature 34 defines a small jaw space and only a slight defection of the clamping spring 26 is required to reach the locked position. Consequently the grasping force applied to the ligature is low reducing the possibility of damaging the ligature.

Figure 4:
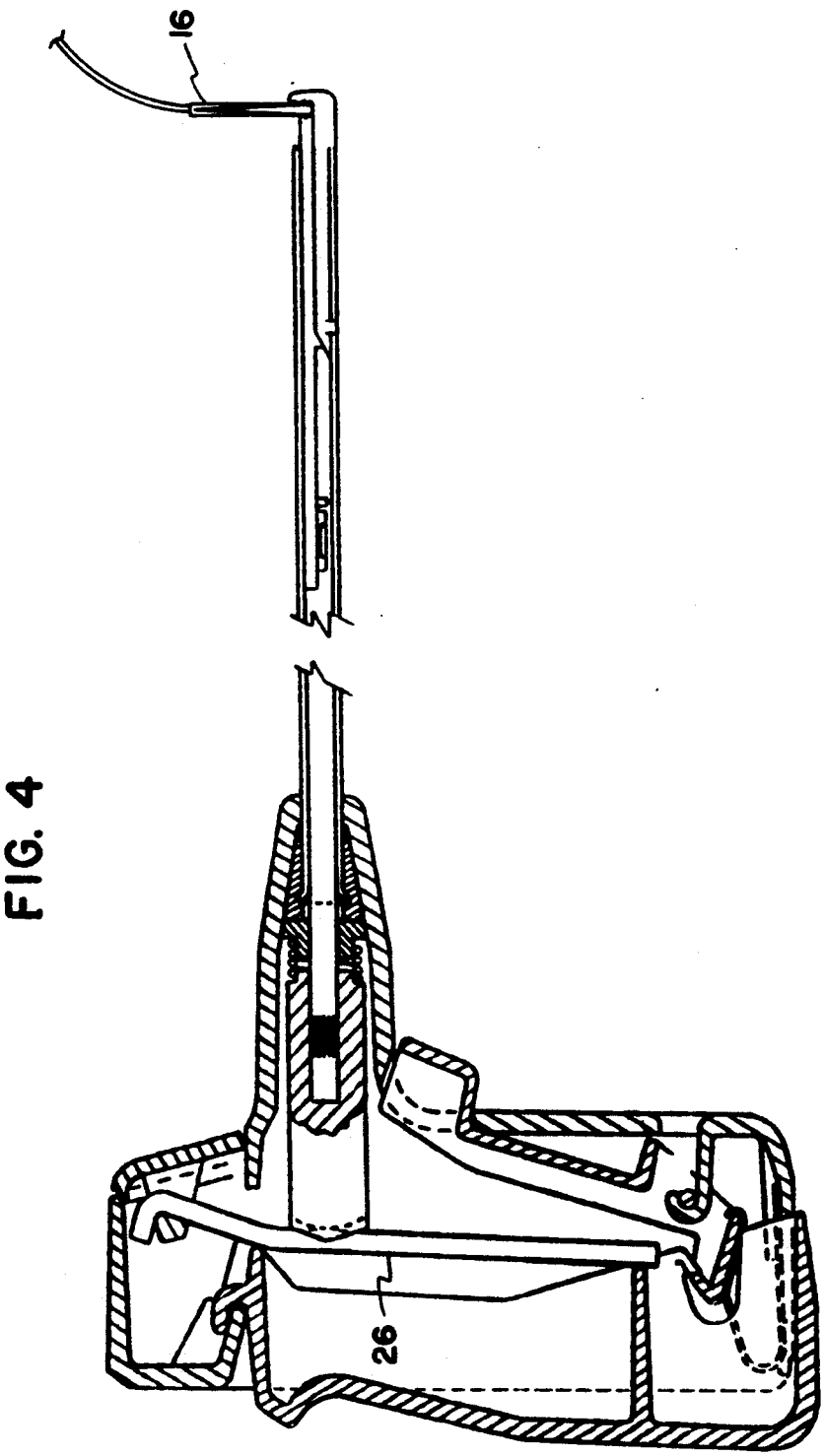
FIG. 4 is a cross-section of the surgical instrument depicting the jaws closed on a surgical needle.

FIG. 4 shows the jaws closed onto a needle 16. Here the diameter of the needle across the flats or faces of the needle defines the jaw space. In this instance substantially greater deflection of the clamping spring 26 is required to reach the locked position, resulting in substantially greater grasping force applied to the needle 16.

Although the endoneedle holder 10 can be used successfully with conventional straight or curved needles, it is an advantage to use the instrument with a needle having a pair of flattened sides diametrically oppose across the diameter of the needle. A preferred curved needle is depicted in exaggerated scale in FIG. 5. This needle has a radius of approximately 0.5 inches and has a distal end 41 and a proximal end 42. The distal end has an essentially circular cross-section as shown in FIG. 6. The distal end has a complex crossection resulting from the attachment of the needle 16 to the ligature 34. Beginning very near the proximal end the needle crossection takes an approximately ellipsoidal shape, having a major axis 43 and a minor axis 44. This shape is depicted in FIG. 7. The "flattened sides" of the needle 45 and 46 are substantially planar and parallel to each other. These parallel surfaces are also parallel to the plane of the curvature of needle and they help orient the needle in the jaws 13 and 15. The "rounded sides" of the needle are shown as surfaces 47 and 48. The rounded sides in cooperation with the flattened sides cooperate to align or index the needle with respect to the jaws 13 and 15. Although there is great flexibility in the actual cross-sectional shape of the needle between the jaws a conventional needle of approximately 0.042 inches may be rolled to flattened the needle generating a minor diameter of approximately 0.036 inches, to produce a useful needle. In endoscopic surgical operations the limited depth of field renders it difficult to accurately align the plane of the curvature of the needle with the jaw position. It is usually preferable to have the plane of the curvature of the needle to be perpendicular to the axis of the sheath, so that rotation of the instrument passes the needle through the tissue mass without applying torque to the tissue mass itself, the specialized crossection of the needle near the proximal end 42 materially aid rapid and confident use of the endoneedle holder instrument 10.

MATERIALS

There is great flexibility in the selection of materials for the various components of the endoneedle holder. However it is preferred to mold the plastic components from medical grade polysulfone plastic. It is preferred to form the metal components such as the sheath, clamping spring, push rod and jaw members from type 303 or type 304 stainless steel. The gas seal may be formed from Kraton elastomer. Each of these materials may be sterilized using conventional techniques.

What is claimed:

1. A surgical instrument for grasping an object comprising:
    a control handle having a fixed grip and having a movable grip;
    an elongate sheath having a lumen, connected to said fixed grip;
    a fixed jaw coupled to said sheath, said fixed jaw not extending radially beyond said sheath;
    a movable jaw located within said sheath proximate said fixed jaw, said movable jaw not extending radially beyond said sheath;
    said movable jaw and said fixed jaw together defining a variable jaw space, said jaw space having a cross section which does not substantially exceed the cross section area of said lumen;
    clamping spring means coupled to said movable grip and coupled to said moveable jaw for transferring clamping force from said moveable grip to said object located within said variable jaw space;
    whereby motion of said movable grip reduces said variable jaw space and causes said object to abut said movable jaw and said fixed jaw and whereby the force imparted by said moveable grip is imparted to said object and wherein continued motion of said moveable grip deflects said clamping spring means which applies a clamping force to said object proportional to the size of said object in said jaw space, and said clamping force increases with deflection of said clamping spring means;
    lock means for preventing motion of said movable grip when said lock means is in a first locked position and for permitting motion of said movable grip when said lock means is in a second unlocked position.

2. A surgical instrument for grasping an object comprising:
a control handle having a fixed grip and having a movable grip;
an elongate sheath having a lumen, connected to said fixed grip;
a fixed jaw coupled to said sheath;
a movable jaw located within said sheath proximate said fixed jaw;
said movable jaw and said fixed jaw together defining a variable jaw space;
clamping spring means coupled to said movable grip and coupled to said moveable jaw for transferring clamping force from said moveable grip to said object located within said variable jaw space;
whereby motion of said movable grip reduces said variable jaw space and causes said object to abut said movable jaw and said fixed jaw and whereby the force imparted by said moveable grip is imparted to said object and wherein continued motion of said moveable grip deflects said clamping spring means which applies force to said object proportional to the size of said object in said jaw space;
lock means for preventing motion of said movable grip when said lock means is in a first locked position and for permitting motion of said movable grip when said lock means is in a second unlocked position, said lock means including;
a release button member pivotally mounted in said fixed grip, said release button member having a latch hasp;
a latch hook coupled to said moveable grip;
whereby said moveable grip engages said latch hasp with said latch hook defining a fixed locked position, and whereby said clamping spring generates a gripping force proportional to said jaw space when said moveable grip is in said fixed locked position.

3. A surgical instrument for grasping objects comprising:
a control handle having a fixed grip and having a movable grip;
an elongate sheath having a lumen, connected to said fixed grip;
a fixed jaw coupled to said sheath;
a movable jaw located within said sheath proximate said fixed jaw;
said movable jaw and said fixed jaw together defining a jaw space;
clamping spring means coupled to said movable grip and coupled to said moveable jaw for supplying clamping force to objects located within said jaw space;
a release button member pivotally mounted in said fixed grip, said release button member having a latch hasp;
a latch hook coupled to said moveable grip;
whereby said moveable grip engages said latch hasp with said latch hook defining a fixed locked position, and whereby said clamping spring generates a gripping force proportional to said jaw space when said moveable grip is in said fixed locked position.

4. A surgical instrument for grasping an object comprising:
a control handle having a fixed grip and having a movable grip;
an elongate sheath having a lumen, connected to said fixed grip;
a fixed jaw coupled to said sheath;
a movable jaw located within said sheath proximate said fixed jaw;
said movable jaw and said fixed jaw together defining a variable jaw space;
clamping spring means coupled to said movable grip and coupled to said moveable jaw for transferring clamping force from said moveable grip to said object located within said variable jaw space;
whereby motion of said movable grip reduces said variable jaw space and causes said object to abut said movable jaw and said fixed jaw and whereby the force imparted by said moveable grip is imparted to said object and wherein continued motion of said moveable grip deflects said clamping spring means which applies force to said object proportional to the size of said object in said jaw space;
lock means for preventing motion of said movable grip when said lock means is in a first locked position and for permitting motion of said movable grip when said lock means is in a second unlocked position;
said fixed jaw coupled to said sheath, having a firsts jaw face;
said movable jaw located within said sheath proximate said fixed jaw, having a second jaw face;
said first jaw face being parallel to said second jaw face.

5. The surgical instrument of claim 4 wherein:
said first jaw face being parallel to said second jaw face, and both said first jaw face and said second jaw face being substantially perpendicular to the major axis of said sheath.

6. A surgical instrument for grasping an object comprising:
a control handle having a fixed grip and having a movable grip;
an elongate sheath having a lumen, connected to said fixed grip;
a fixed jaw coupled to said sheath;
a movable jaw located within said sheath proximate said fixed jaw;
said movable jaw and said fixed jaw together defining a variable jaw space;
clamping spring means coupled to said movable grip and coupled to said moveable jaw for transferring clamping force from said moveable grip to said object located within said variable jaw space;
whereby motion of said movable grip reduces said variable jaw space and causes said object to abut said movable jaw and said fixed jaw and whereby the force imparted by said moveable grip is imparted to said object and wherein continued motion of said moveable grip deflects said clamping spring means which applies force to said object proportional to the size of said object in said jaw space;
lock means for preventing motion of said movable grip when said lock means is in a first locked position and for permitting motion of said movable grip when said lock means is in a second unlocked position;
said clamping spring means including
a clamping spring having a first end and having a second end;

said first end pivotally mounted in said fixed grip, and said second end being mounted in said movable grip;

said movable grip pivotally mounted in said fixed grip, and adapted for partial rotation about said fixed grip;

said clamping spring being coupled to said movable jaw;

whereby motion of said movable grip about said fixed grip causes said clamping spring to move about said pivotal mount in said fixed grip, whereby motion of said movable grip causes motion of said movable jaw.

7. The surgical instrument of claim 6 wherein said lock means comprises:
  a release button member pivotally mounted in said fixed grip, said release button member having a latch hasp;
  a latch hook coupled to said moveable grip;
  whereby said moveable grip engages said latch hasp with said latch hook defining a fixed locked position, and whereby said clamping spring generates a gripping force in said jaw space, proportional to the deflection of said clamping spring when said movable grip is in said fixed locked position.

8. A surgical instrument for grasping objects comprising:
  a control handle having a fixed grip and having a movable grip;
  an elongate sheath having a lumen, connected to said fixed grip;
  a fixed jaw coupled to said sheath;
  a movable jaw located within said sheath proximate said fixed jaw;
  said movable jaw and said fixed jaw together defining a jaw space;
  clamping spring means coupled to said movable grip and coupled to said moveable jaw for supplying clamping force to objects located within said jaw space;
  a grip locking means for defining a lock position for said control handle, and whereby said clamping spring generates an increasing clamping force proportional to said jaw space when said moveable grip is moved toward said lock position.

* * * * *

UNITED STATES PATENT AND TRADEMARK OFFICE
CERTIFICATE OF CORRECTION

PATENT NO. : 5,300,082

DATED : Apr. 5, 1994

INVENTOR(S) : Sharpe et al.

It is certified that error appears in the above-indentified patent and that said Letters Patent is hereby corrected as shown below:

In column 2, line 57, please delete the word "crossection" and insert therefor --cross-section--

In column 3, line 14, after the word "formed", please insert the word --in--

In column 3, line 32, please delete the word "has" and insert therefor --hasp--

In column 3, line 57, please delete the word "oppose" and insert therefor --opposed--

In column 3, line 63, please delete the word "crossection" and insert therefor --cross-section--

In column 3, lines 65 and 66, please delete the word "crossection" and insert therefor --cross-section--

In column 4, line 11, please delete the word "flattened" and insert therefor --flatten--

UNITED STATES PATENT AND TRADEMARK OFFICE
CERTIFICATE OF CORRECTION

PATENT NO. : 5,300,082

DATED : Apr. 5, 1994

INVENTOR(S) : Sharpe et al.

It is certified that error appears in the above-indentified patent and that said Letters Patent is hereby corrected as shown below:

In column 4, lines 20 and 21, please delete the word "crossection" and insert therefor --cross-section--

In column 4, line 53, before the word "coupled", please insert the words --said spring clamping means--

In column 5, line 15, before the word "coupled", please insert the words --said spring clamping means--

In column 5, line 53, before the word "coupled", please insert the words --said spring clamping means--

In column 6, line 9, before the word "coupled", please insert the words --said spring clamping means--

In column 6, line 26, please delete the word "firsts" and insert therefor --first--

In column 6, line 49, before the word "coupled", please insert the words --said spring clamping means--

UNITED STATES PATENT AND TRADEMARK OFFICE
CERTIFICATE OF CORRECTION

PATENT NO. : 5,300,082

DATED : Apr. 5, 1994

INVENTOR(S) : Sharpe et al.

It is certified that error appears in the above-indentified patent and that said Letters Patent is hereby corrected as shown below:

In column 6, line 66, after the word "including", please insert a colon --:--

In column 8, line 15, before the word "coupled", please insert the words --said spring clamping means--

Signed and Sealed this

Eighth Day of November, 1994

Attest:

BRUCE LEHMAN

Attesting Officer

Commissioner of Patents and Trademarks